United States Patent [19]

McDonald et al.

[11] Patent Number: 5,728,150
[45] Date of Patent: Mar. 17, 1998

[54] EXPANDABLE MICROPOROUS PROSTHESIS

[75] Inventors: Edward A. McDonald, Irvine; Robert Rosenbluth, Laguna Niguel; Rodney Brenneman, San Juan Capistrano, all of Calif.

[73] Assignee: Cardiovascular Dynamics, Inc., Irvine, Calif.

[21] Appl. No.: 754,816

[22] Filed: Nov. 21, 1996

Related U.S. Application Data

[63] Continuation-in-part of Ser. No. 681,906, Jul. 29, 1996, Pat. No. 5,676,697.

[51] Int. Cl.$^6$ .................................................. A61F 2/06
[52] U.S. Cl. .................................................. 623/1; 623/12
[58] Field of Search .................................................. 623/1, 11, 12

[56] References Cited

U.S. PATENT DOCUMENTS

| | | |
|---|---|---|
| Re. 34,327 | 7/1993 | Kreamer . |
| 4,665,918 | 5/1987 | Garza et al. . |
| 4,739,762 | 4/1988 | Palmaz . |
| 4,740,207 | 4/1988 | Kreamer . |
| 4,776,337 | 10/1988 | Palmaz . |
| 4,800,882 | 1/1989 | Gianturco . |
| 4,877,030 | 10/1989 | Beck et al. . |
| 4,922,905 | 5/1990 | Strecker . |
| 5,007,926 | 4/1991 | Derbyshire . |
| 5,059,211 | 10/1991 | Stack et al. . |
| 5,078,726 | 1/1992 | Kreamer . |
| 5,089,006 | 2/1992 | Stiles . |
| 5,100,429 | 3/1992 | Sinofsky et al. . |
| 5,167,614 | 12/1992 | Tessmann et al. . |
| 5,171,262 | 12/1992 | MacGregor . |
| 5,192,307 | 3/1993 | Wall . |
| 5,234,448 | 8/1993 | Wholey et al. . |
| 5,242,399 | 9/1993 | Lau et al. . |
| 5,254,127 | 10/1993 | Wholey et al. . |
| 5,266,073 | 11/1993 | Wall . |
| 5,306,286 | 4/1994 | Stack et al. . |
| 5,306,294 | 4/1994 | Winston et al. . |
| 5,344,426 | 9/1994 | Lau et al. . |
| 5,354,309 | 10/1994 | Schnepp-Pesch et al. . |
| 5,366,473 | 11/1994 | Winston et al. . |
| 5,383,926 | 1/1995 | Lock et al. . |
| 5,405,379 | 4/1995 | Lane . |
| 5,411,549 | 5/1995 | Peters . |
| 5,411,551 | 5/1995 | Winston et al. . |
| 5,423,885 | 6/1995 | Williams . |
| 5,441,515 | 8/1995 | Khosravi et al. . |
| 5,443,500 | 8/1995 | Sigwart . |
| 5,449,382 | 9/1995 | Dayton . |
| 5,540,713 | 7/1996 | Schnepp-Pesch et al. . |

OTHER PUBLICATIONS

Scanning Electron Microscopy Evaluation of Porous and Nonporous Arterial Substitutes. Giovanni B. Ratto, M.D., Carmen Lunghi, M.D. Enzo Spinelli, M.D., Riccardo Agati, M.D. Marzia Tomellini, M.D., and Giovanni Motta, M.D., Genoa, Italy, Surgery, Gynecology & Obstetrics, Sep. 1982, vol. 155.

(List continued on next page.)

*Primary Examiner*—Michael J. Milano
*Attorney, Agent, or Firm*—Knobbe, Martens, Olson & Bear, LLP

[57] ABSTRACT

Disclosed is a tubular prosthesis formed by rolling a perforated sheet around a longitudinal axis. Preferably, the prosthesis is self expandable under the radially outwardly directed spring bias of the rolled sheet. The perforations in the sheet are configured to provide throughholes in the wall of the multilayer prosthesis, when the prosthesis is in the implanted diameter within a vessel. The throughholes are configured to facilitate neointimal cell growth, and in a preferred embodiment, to minimize roll bias in the prosthesis as it is expanded from its reduced, insertion diameter to its expanded, implanted diameter. The prosthesis may be used as a graft or a stent.

26 Claims, 3 Drawing Sheets

OTHER PUBLICATIONS

Morphology of Healing in Vascular Prosthesis, G. Rahlf P. Urban, and R.M. Bohle, Read at the 14th Annual Meeting of the German Society for Thoracic and Cardiovascular Surgery, Bad Nauheim 1985, Thoracic Cardiovascular Surgeon 34 (1986).

Endothelial Cell Adhesion to Vascular Prosthetic Surfaces, D. Gourevitch, Carolyn E. Jones, J. Crocker and M. Goldman, Presented at Biointeractions —87, Cambridge, UK in Jul. 1987, Biomaterials 1988, vol. 9, Jan.

Restenosis After Balloon Angioplasty, A Practical Proliferative Model in Porcine Coronary Arteries, Robert S. Schwartz, MD, Joseph G. Murphy, MB, William D. Edwards, MD, Allan R. Camrud RN, Ronald E. Vlietstra, MB, BCh, and David R. Holmes, MD, Circulation, vol. 82, No. 6, Dec. 1990.

EXPANDABLE MICROPOROUS PROSTHESIS

CROSS-REFERENCE TO RELATED APPLICATION

This is a continuation-in-part of commonly assigned, U.S. patent application Ser. No. 08/681,906 filed Jul. 29, 1996, now U.S. Pat. No. 5,676,697, for two-piece, bifurcated intraluminal graft for repair of aneurysm in the name of Edward A. McDonald.

FIELD OF THE INVENTION

The present invention relates to an intraluminal graft or stent that is adapted to be advanced in a collapsed roll to the site of an aneurysm, defect or injury of a body vessel and expanded or allowed to self expand across the site in an expanded roll, and particularly to such a graft or stent formed of a porous sheet enabling neointimal tissue ingrowth therethrough to stabilize the stent at the site.

BACKGROUND OF THE INVENTION

In numerous medical and surgical techniques, stents, grafts, or stent-grafts hereinafter sometimes referred to as implantable tubular prostheses, are inserted into body vessels or ducts or the like, temporarily or permanently, in order to repair a defect or maintain the patency of the vessel or duct lumen to as great a degree as possible. Transluminal implantation of such prostheses requires that they be introduced to the site collapsed about or within an introduction device and released to self expand or are expanded by other mechanisms to an expanded tubular state providing a lumen of approximately the same size as the patent vessel or duct lumen.

A wide variety of such tubular prostheses have been proposed for introduction through a percutaneous access site and advancement through the vascular system to an aneurysm, defect or injury site and for deployment to bridge the site. Once deployed in situ, the prosthesis must be stabilized mechanically until neointimal growth occurs over the graft ends and interior surface. Such prostheses have been formed of a wide variety of materials and shapes to accommodate particular vascular sites and to encourage neointimal growth. In addition, a wide variety of deployment mechanisms and techniques have been proposed to position and stabilize the prosthesis in place including "active" fixation mechanisms designed to penetrate the vessel wall and "passive" fixation mechanisms that press against and expand the diameter of the vessel lumen.

For example, certain expandable metal "wire stents" have been employed in clinical use for insertion into an artery in order to assist in preventing re-stenosis after a balloon angioplasty procedure has been completed to expand a stenosed site. These wire stents are relatively structurally stiff, and when expanded at the site (typically by a further balloon catheter) engage the previously (or simultaneously) compressed remnant of the occlusion in the vessel and are passively retained in place by friction until neointimal growth permanently encases the stent. Typically, such wire stents are formed of wire mesh or wire loops or are formed of a perforated metal sheet, as shown, for example, in U.S. Pat. Nos. 4,776,337, 4,877,030, 5,007,926, and 5,079,006. Such wire stents have relatively large openings in the side wall thereof in relation to the wire gauge or remaining sheet material bounding the openings. After insertion to the site of implantation, the inner diameter of the tubular wire stent can be expanded by a balloon catheter or the like into engagement with the vessel wall. The large openings result from the attempt to minimize the number of wire strands and turns of the stent, because, after expansion in situ, each exposed turn or strand slightly intrudes into the vessel lumen and causes perturbation in the blood flow and can constitute a site of formation of blood clots.

Such wire stents are formed of a single layer of wire mesh or strand in either a tubular form or a rolled sheet form. When the rolled sheet form is expanded, only a minor overlap if any of adjoining edges is contemplated as shown in the structures shown in the '030, '006 and '926 patents. The resulting stent structure is porous, but blood flow through the openings between wire turns or through the perforations is not an issue because the openings or perforations bear against the vessel wall. The blood contact or circulation alongside the openings or perforations encourages neointimal ingrowth to stabilize the stent. However, the relatively large openings can also allow fibrotic build-up to occur through the openings and possibly constrict the wire stent lumen over time. In addition, the relatively large openings are not very effective in repairing other defects in the vessel wall, e.g., a tear or dissection, thus limiting the uses of such stents.

At this point, it should be pointed out that at times, the term "stent" is used interchangeably in the prior art with "graft," although vascular grafts classically are longer and have less porous side walls than the above-described wire stent. The expression "vascular graft" originally was used to described harvested blood vessels used to bypass a length of diseased or enlarged blood vessel, and the expression "artificial graft" typically connotes an elongated, biocompatible, tubular body mimicking the flexibility of the natural blood vessel it is intended to replace. In an open chest surgical procedure, the active attachment of such flexible vascular or artificial grafts to patent blood vessel ends is effected by suturing in a procedure referred to as anastomosis.

Elongated, artificial "intraluminal grafts" have also been developed for use in an intraluminal implantation procedure to bridge elongated aneurysms, defects or injuries to avoid invasive vascular surgery. Such intraluminal grafts are typically formed of a single tube of flexible biocompatible materials, e.g., a Dacron fabric tube that is long enough or shaped especially to bridge the defective region of the blood vessel, coupled with one or more retention mechanism at an end or ends thereof. Certain of the retention mechanisms proposed for use with such intraluminal grafts employ passive stents at each end that are allowed to self expand or are expanded to enlarge and frictionally engage patent vessel wall on either side of the site as shown, for example, in U.S. Pat. No. 3,991,767. The end stents may alternatively include active barbs or hooks that are manipulated to invade the patent vessel wall and retain the graft in position. Such combinations of stent and graft structures are at times referred to as "stent-grafts" and are also shown, for example, in U.S. Pat. Nos. 5,078,726 and 5,336,473.

Another artificial intraluminal stent that is typically not porous and may be used to bridge a defect or maintain the patency of an expanded vessel lumen is formed as a tubular body from a sheet of biocompatible metal, plastic or other material. The sheet metal is rolled up in a collapsed roll state in one or more overlapping layers that can be advanced intraluminally and expanded to bridge the site. Examples of such intraluminal stents and introduction systems are shown, for example, in U.S. Pat. No. Re34,327, U.S. Pat. Nos. 4,740,207, 5,100,429, 5,306,294 and 5,405,379. Such stents are also employed as the end fixation mechanisms in stent-grafts as shown in certain embodiments of the above-referenced '726 and '473 patents.

The stents disclosed in the above-referenced '473 and '294 patents are advantageous in that they are formed of a sheet of metal foil adapted to be rolled into a plurality of sheet layers forming the collapsed and expanded rolls that are radiopaque and allow visualization of their advancement and deployment at the site. Moreover, when released at the site, no separate expansion mechanism is required because the rolled up sheet material self expands to a size that fits and slightly expands the lumen of the vessel or duct. The stent or stent-graft is retained by passive engagement of the expanded roll of sheet material against the vessel or duct lumen caused by the expansion spring force tending to further expand the diameter of the expanded tubular member. As a result of the self expansion spring force and the expansion range, sizing of the expanded tubular body diameter to the vessel or duct lumen is not critical. The multiple overlapping layers ensure that no gap can occur between the opposite edges of the sheet. Moreover, the rolled, overlapping layers forming the side wall of the stent provides substantial hoop strength to resist or prevent re-stenosis in the vessel wall. Certain of these advantages are also obtained by the nortradiopaque stent depicted in the above-referenced '579 patent.

In such self expanding (or balloon expandable) multiple layer side wall stents formed of rolled sheet material as described in the above-referenced patents, the nonporous smooth inner lumen advantageously does not create flow perturbations along its length. On the other hand, the impervious side wail formed by the roll of sheet material is likely to limit the area of neointimal growth within the stent lumen to about 0.125 inches from each end opening. Consequently, over a period of days or weeks, blood clots may be encouraged to form by contact with the exposed sheet material of the inner lumen surface. The blood clots can break away and migrate to a site posing a danger to the patient. It may therefore be necessary to suppress clot formation with anticoagulant drags, e.g., coumarin, aspirin, or others, for extended indefinite periods of time in the case of solid sheet material stents.

Thus there remains a need for an improved self expandable intraluminal prosthesis designed to encourage neointimal-tissue ingrowth and suitable for use as a vascular graft.

SUMMARY OF THE INVENTION

In accordance with one aspect of the present invention, there is provided an intraluminal prosthesis adapted to be introduced to a site in a body vessel in a collapsed roll state and implanted to bridge the site in an expanded roll state, the stent comprising: a tubular body having a side wall and an inner lumen of an axial length extending in a longitudinal direction between first and second ends, the tubular body formed of a sheet of biocompatible material rolled into a plurality of overlapping layers to form the tubular body side wall and inner lumen, the sheet having a sheet width corresponding to the tubular body axial length and a sheet length providing the plurality of overlapping layers when in the expanded roll state; and one or more perforation zones formed in the sheet and spaced apart along the length thereof adapted to substantially overlie one another when the sheet is rolled into the plurality of layers in the expanded roll state, the perforation zones occupying substantially equal areas of the sheet, and each perforation zone further comprising a plurality of perforations extended in parallel with one another at a predetermined perforation angle to the sheet length, wherein the perforation angle of the elongated perforations of every other perforation zone along the length of sheet, whereby the plurality of perforation zones substantially overlie one another when the sheet is rolled into the tubular body side wall having a substantially corresponding plurality of layers and provide holes extending through the tubular body side wall where portions of the elongated perforations overlie one another in the sheet layers rolled up to form the side wall to encourage the formation of neointimal growth in the tubular body lumen between the adjacent holes.

For example, prostheses designed to form two, three or four overlapping layers or any fraction thereof when expanded in situ to the expanded roll state preferably have two, three or four perforation zones, respectively, extending along the length of the sheet and separated from one another and the sheet edge by solid border bands. Each perforation zone is substantially the same size and has substantially an equal number of elongated perforations each extending at differing angles to one another. The overall length of the sheet is dependent upon an average circumference in a range of circumferences of body lumens intended to be accommodated by the stent in the expanded roll state multiplied by the desired number of overlapping layers of the tubular body side wall. The dimensions of each perforation zone are set by the average circumference and by the width of the sheet.

When the elongated perforations of the perforation zones in the outer or inner layer of the tubular body have perforation angles that are at an acute angle to the sheet length direction, a curl bias can occur in the expanded roll state tending to cause the sheet to roll up at a 90° angle to the angle of the perforation angle. To counter this tendency, the sheet is preferably further subdivided into first and second halves by a center band extending along the length thereof with each half having an equal number of perforation zones arranged in side by side relationship across the center band. The perforation angles of the elongated perforations in the perforation zones separated by the center band are chosen to be complementary to one another such that any curl biases induced by the perforation angles in each half offset or counter each other, thereby ensuring that the sheet roll ups into the tubular body in the expanded roll state in the direction of the sheet length.

The resulting holes through the tubular body side wall in the expanded roll state may be characterized as microperforations and can have a somewhat tortuous path depending on how tightly the adjoining sheet layers contact one another. The resulting holes vary in size depending on the degree of coincidence of overlapping elongated perforations and are no larger in size than the width of any one of the elongated perforations. The resulting spacing between adjoining holes may be irregular and depends on the number of overlapping layers. The sizes and spacings of the holes and the tortuosity of the hole paths through the overlapping layers approaches those present in typical synthetic woven or knitted graft material, e.g., woven Dacron fabric.

Preferably the border bands are minimized to allow neointimal growth across them, and the pairs of perforation zones in the sheet halve occupy substantially the entire sheet. However, the border bands prevent the elongated perforations of each zone from encroaching on the elongated perforations of adjacent zones or reaching the edges of the sheet to preserve the sheet integrity.

The preferred embodiment of the stent of the present invention is self expanding from the collapsed roll state during introduction to the expanded roll state in situ and is not provided with any active fixation mechanism. The microperforations embedment of vessel walls cells into the holes of the tubular body side wall upon deployment and increases resistance to dislodgment or movement from the site during the acute phase of neointimal ingrowth.

Although the sheet is preferably formed of metal foil, the invention may be practiced using sheets formed of biocompatible plastic materials or other suitable sheet materials.

These and other advantages and features of the invention will become apparent from the following detailed description of the preferred embodiments of the invention.

Figure 1:
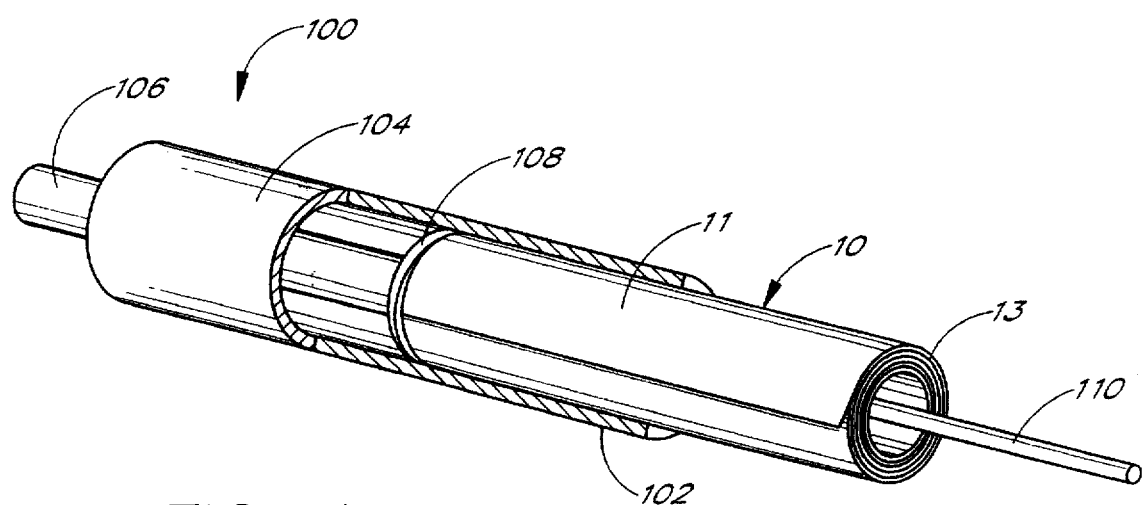
FIG. 1 is a fragmentary perspective view of a stent in accordance with the present invention and the distal end of one exemplary form of a placement system for placing the stent in its collapsed roll state at a desired site in a body lumen.

The drawing figures are not necessarily to scale.

DETAILED DESCRIPTION OF THE PREFERRED EMBODIMENT

The present invention is described in the context of a preferred embodiment of a tubular graft for intraluminally bridging an aneurysm, defect or injury or for supporting and maintaining a vessel lumen at the site of a stenotic lesion from restenosis following an angioplasty or other procedure for opening a blood vessel lumen. It will be understood that the invention may be incorporated into prostheses of all types for maintaining patency of lumens of blood vessels or other body ducts or vessels and that the expression "body lumen" includes all such lumens.

Turning to FIG. 1, it depicts a prosthesis 10 constructed in accordance with a preferred embodiment of the invention in relation to an exemplary stent placement system 100 that may be used to intraluminally introduce and release the stent 10 at a desired body site. Alternate deployment systems and useful deployment methods are disclosed in U.S. Pat. Nos. 5,405,379; 5,306,294 and 5,336,473, the disclosures of which are incorporated herein by reference.

The stent 10 is shown in its retracted state and partially deployed from the distal end 102 of a tubular introducer catheter 104. The illustrated introducer catheter 104 has an inside diameter substantially equal to the outer diameter of the stent 10 when in its collapsed roll state. The catheter 104 is provided with at least one elongate lumen extending axially therethrough, for removably receiving a pusher 106. In the illustrated embodiment, pusher 106 comprises an elongate flexible tubular element having an outside diameter which is less than the inside diameter of the catheter 104. The pusher 106 is therefore preferably provided with a stop 108 on the distal end thereof for permitting the pusher 106 to efficiently push the prosthesis 10 distally from the catheter 104. Preferably, the catheter 104 is adapted to be introduced over a guidewire 110, which is axially slidably received through the coiled prosthesis 10 and through the lumen within pusher element 106.

As shown in FIG. 1, the prosthesis or stent 10 is formed of a sheet 11 that is rolled up into a tubular body 13 of multiple Overlapping layers of sheet 11. The tubular body 13 therefore has a side wall formed of the multiple rolled up layers of sheet 11, an inner lumen around the guide wire 110, and an axial length extending, in the longitudinal direction of the introducer catheters 104 between proximal and distal tubular body ends. The proximal tubular body end butts against the stop 108, and the distal tubular body end will generally be positioned near the distal end 102 of catheter 104. The guide wire 110 guides introduction of the distal end 102 of the outer introducer catheter 104 including the stent 10 within it to a body tureen site for deployment of the stent 10 in a manner generally taught in the above-referenced '294 and '473 patents, incorporated herein by reference in their entireties.

The reduced implantation diameter of the tubular body 13 is dictated by the inside diameter of the catheter 104. In an alternative embodiment of the placement system 100 such as that disclosed in the '294 patent, the outer sheath 104 is not used and cords (not shown in FIG. 1) are used to restrain the sheet 11 in the collapsed roll state until the cords are withdrawn all in a manner taught in the above-incorporated '294 patents.

In accordance with a method of installation using the depicted placement system 100, the perforated sheet 11 is rolled up into a tubular stent 13 such as by rolling the sheet 11 around a mandril (not illustrated). The rolled tubular body 13 is then loaded into the distal end 102 of the introduction catheter 104, either at a point of manufacture, or at the clinical site. The radially outwardly directed bias of the tubular body 13, as discussed in greater detail infra, causes the tubular body 13 to press radially outwardly against the interior wall of the catheter 104, thereby retaining the tubular body 13 in position within the catheter 104. The introducer catheter 104 and the stent 10 are thereafter introduced over the guide wire 110 and advanced transluminally to the desired body lumen site with the tubular body 13 restrained in the collapsed roll state. At the site, the pusher 106 is advanced distally with respect to the catheter 104 to expel the stent 10 out of the distal end opening of catheter 104. Preferably, the catheter 104 is withdrawn proximally while the pusher 106 is maintained stationary in the vessel. The released tubular body 13 self expands in diameter to its expanded roll state constrained in size by the diameter of the body lumen at the site.

The placement system 100 of FIG. 1 and the method of placement described above provide one example of a system and method for collapsing the stent 10 and for effecting its introduction and release at the site that may be employed with the improved stent 10 of the present invention. Any of a variety of alternate deployment systems can also be used as will be apparent to persons of skill in the art in view of the disclosure herein.

Moreover, the perforation pattern of the stent sheet of the present invention may be incorporated into stents that are not self expanding and are expanded at the site by expansion mechanisms. In such a case, the stent expanded roll state would still have multiple layers of the sheet in the side wall thereof as shown in the remaining figures.

Returning to FIGS. 1–3, the tubular body 13 is formed of a sheet 11 of biocompatible material rolled into a plurality of layers to form the side wall and a central lumen. The tubular body 13 therefore presents a plurality of adjacent arcuate layers of the sheet 11 rolled up in a direction transverse to the longitudinal direction and the longitudinal axis of the stent 10. The sheet 11 possesses an inherent resilience and spring force that seeks to unwind the wound layers and expand the stent lumen as described in the above-incorporated '294 patent, for example. In the fully expanded roll state of the illustrated preferred embodiment within a vessel, there are at least two to three fully overlapping layers that bear against one another under the spring force.

Figure 2:
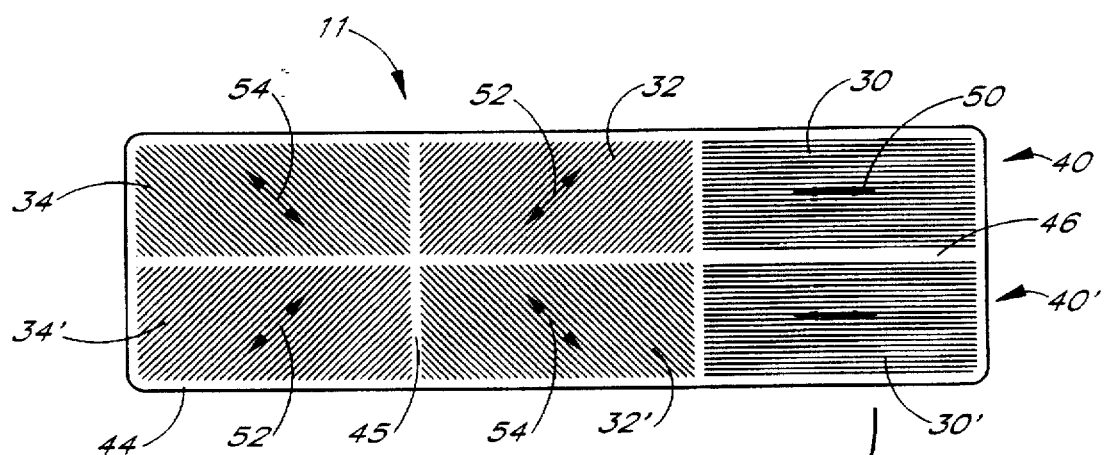
FIG. 2 is a plan view of one sheet pattern from which the stent of the present invention is formed showing the symmetrical orientation of a pair of first, second and third zones of the sheet containing elongated perforations orientated at complementary angles to one another.
Figure 3:
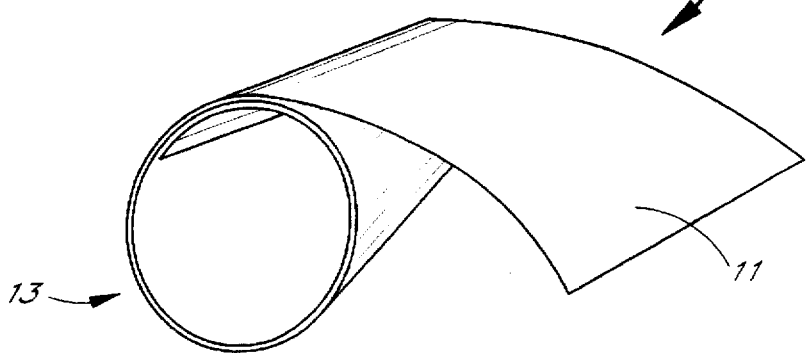
FIG. 3 is a schematic illustration of the sheet of FIG. 2 being rolled into a tubular prosthesis.

Turning to FIG. 2, the sheet 11 is shown flattened out to illustrate the perforation pattern employed in a preferred embodiment of the present invention to assure that openings extend through the multiple layers of the rolled up sheet 11 forming the tubular body 13 in the expanded roll state. The sheet 11 has a sheet length SL providing the plurality of overlapping layers when the sheet 11 is rolled up in the length direction and a sheet width SW corresponding to the axial length of tubular body 13. The sheet width SW and length SL in one 3 cm embodiment are on the order of about 30.0 mm and 116.0 mm, respectively; resulting in a tubular body length of about 30 mm. The sheet 11 may be formed of a biocompatible metal alloy, e.g., Elgiloy, in a foil of a thickness of about 0.0015 inches (about 0.038 mm).

It is contemplated that a sheet 11 having an SL of 116 mm and thickness of about 0.0015 inches may be wound into a collapsed roll state to fit within an introducer sheath lumen of about 3.9 mm in inside diameter and have an inner diameter of about 1.3 mm, in which the number of layers in the tubular member side wall approaches 18. When released in situ, the outer diameter of the tubular member 13 may expand to between 12 mm and 18 mm, resulting in between 3 and 2 layers, respectively, forming the side wall of tubular member 13.

In general, the length of the tubular body 13 (which will normally equal the sheet width of the sheet 11) is selected to optimize performance of the prosthesis in the intended use environment. For example, in an application where the prosthesis is intended to be used as a graft for treating a tubular abdominal aortic aneurysm, the sheet width will generally be within the range of from about 300 mm to about 1000 mm. Preferably, the sheet width is selected to provide a graft having an axial length which is greater than the length of the aneurysm or other diseased site being treated. Preferably, each of the proximal and distal ends of the graft will overlap with healthy vessel for a distance of at least about 10 mm. A relatively greater overlap, such as on the order of 20 mm or greater, may be desirable in straight sections of the aorta, to optimize anchoring and tacking down of the ends of the graft by way of neointimal growth.

The illustrated sheet 11 is provided with a plurality of perforation zones 30, 32, 34 and 30', 32' and 34', arranged in first, second and third positions in first and second mirror image halves 40 and 40', respectively, spaced apart along sheet length SL as shown in FIG. 2. In effect, the perforation zones 30, 32, and 34 are arranged in respective first, second and third portions of the strip in a first row in the first half 40, and the perforation zones 30', 32' and 34' are arranged in respective first, second and third portions of the strip in a second row in the second half 40'. A plurality of elongated perforations 28 (shown in FIG. 6) are formed in each of the generally rectangular perforation zones 30, 32, 34, 30', 32' and 34'. Thus, each line in the parallel interior groups of lines in FIG. 2 represents a row of end-to-end perforations such as those illustrated in an enlarged fashion in FIG. 6.

The first perforation zones 30, 30' are each formed with a first plurality of elongated perforations 28 extending in parallel with one another in a first direction 50 parallel to the longitudinal axis of the sheet 11 and nominally designated as 0°. The second perforation zones 32 and 32' are each formed with a second plurality of elongated perforations 28 extending in second and third directions 52 and 54, respectively, at +45° and −45°, respectively, to the longitudinal axis (the 0° direction 50). The third perforation zones 34 and 34' are formed with a third plurality of elongated perforations 28 extending at 90° to one another in the directions 54 and 52 respectively. In this manner, the perforations 28 in the adjacent perforation zones 32, 32' and 34, 34' are at an angle of 90° to one another and equalize bias forces that arise from the perforation directions 52 and 54 that would tend to cause the sheet 11 to twist when rolled up in the collapsed roll state or as the prosthesis expands to the expanded roll state.

In the illustrated embodiment, each of the three rectangular perforation zones 30, 32, 34 and 30', 32'34' of the first and second halves 40, 40' are of equal size. The widths of each perforation zones are somewhat smaller than one half the sheet width SW allowing for border and center bands of sheet material. The lengths of each perforation zone along the sheet length SL are substantially the same and are chosen in this case to substantially correspond to the chosen or target circumference of the resulting tubular body in the expanded roll state having substantially three overlapping layers.

The perforation zones 30, 32, 34 and 30', 32'34' of the first and second halves 40, 40' are formed inside an edge border band 44 extending all the way around the edge of sheet 11 having a width of about 1.2 or 1.3 mm. Similarly, the adjacent perforation zones in each half 40 and 40' are separated from one another by side border bands 45 having a width of about 1.2 mm–1.3 mm. A center border line area 46 of about the same width extends lengthwise down the center of sheet 11 and divides the sheet 11 into the longitudinally extending first and second halves 40 and 40'.

In this manner, the border bands between the perforation zones are preferably minimized, and the first and second pairs of first, second and third zones occupy substantially the entire sheet 11. However, the border bands do prevent the elongated perforations of each zone from encroaching one another or reaching the edges of the sheet 11 to preserve sheet 11 integrity.

Figure 6:
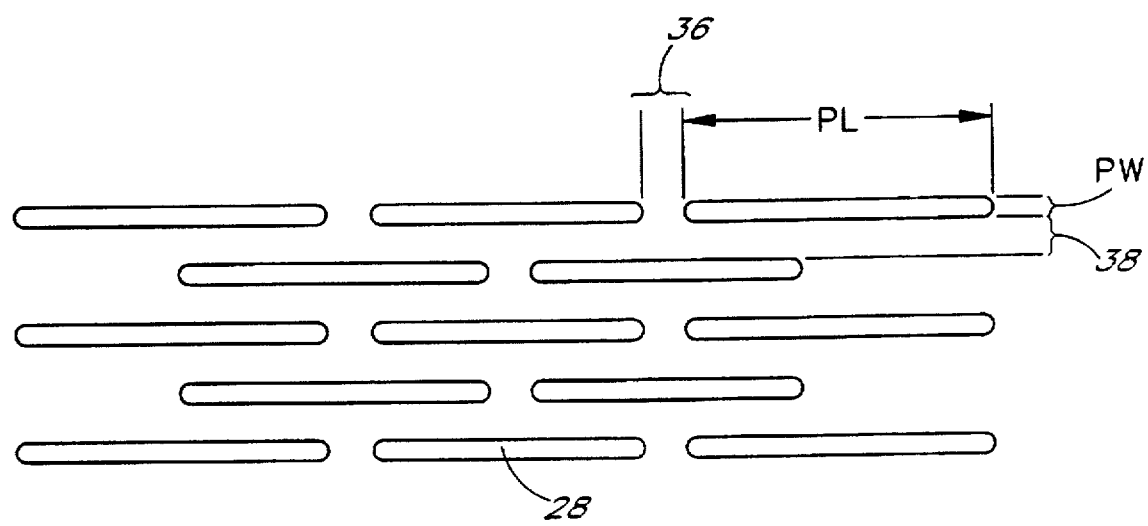
FIG. 6 is an enlargement of a portion of the sheet of FIG. 2, illustrating slot dimensions in accordance with one embodiment of the invention.

Turning to FIG. 6, one perforation pattern of a segment of the plurality of elongated perforations 28 of each zone is shown in enlarged detail. Each elongate perforation 28 is preferably about 3.0 mm in perforation length PL and between 0.10 mm and 0.25 mm in perforation width PW. The end to end and side to side separations 36 and 38 between adjacent perforations 28 is preferably about 0.3–0.4 mm in both cases. The perforations 28 are in parallel with directions 50, 52 and 54 in each of the perforation zones depicted in FIG. 2.

Figure 4:
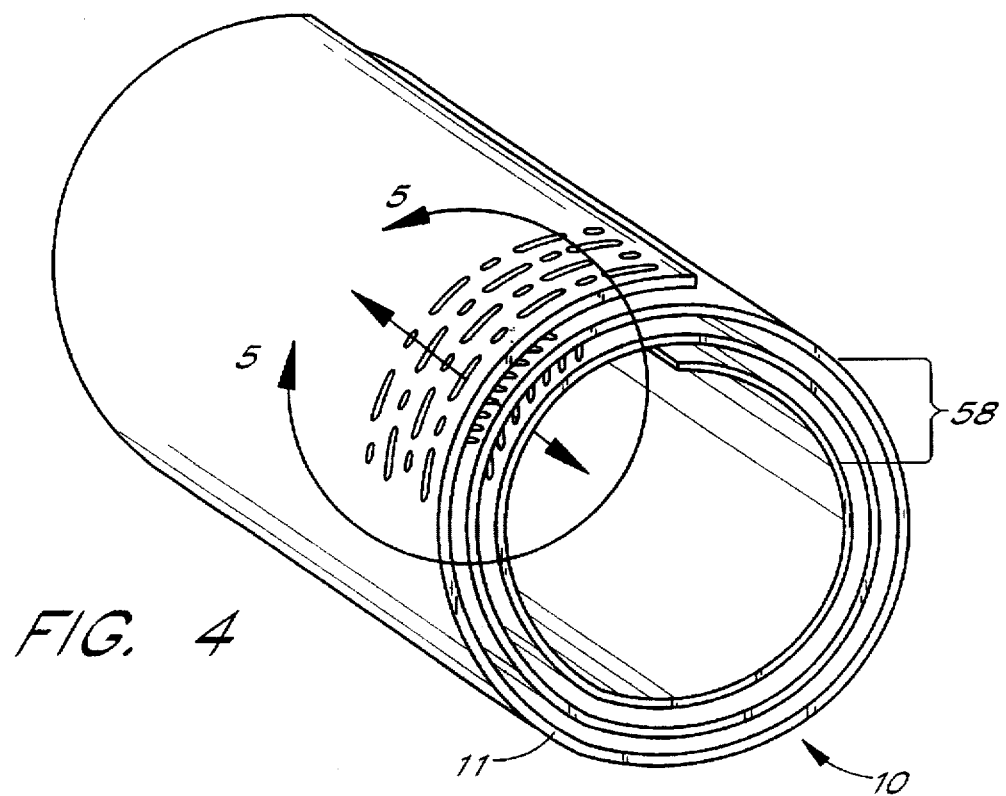
FIG. 4 is an enlarged perspective view of the sheet of FIG. 2 rolled up in a tubular body to form overlapping layers having overlapping zones of perforations.
Figure 5:
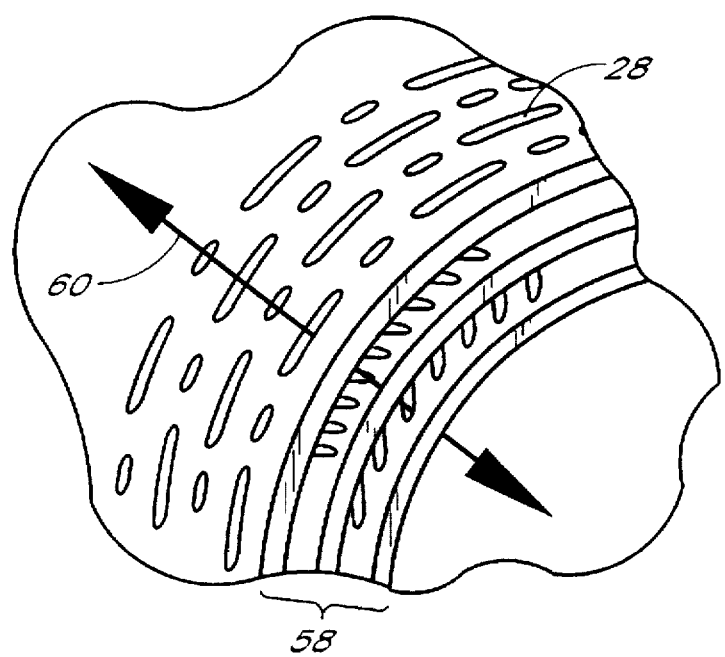
FIG. 5 is a fragmentary enlarged perspective view of a side wall section of three layers of the sheet of FIG. 2 rolled up to overlie one another and depicting alignment of the perforations in the first, second and third perforation zones to provide spaced apart, continuous openings through the side wall.

Turning to FIGS. 4 and 5, the stent 10 of the illustrated embodiment is depicted in one of the possible expanded roll state wherein the sheet 11 is rolled up in the sheet length direction SL in three overlapping rolled up sheet layers which together form the side wall 58 of tubular body 13. Consequently, the perforation zones 30, 32, and 34 in the first half 40 and 30', 32', 34' in the second half 40' overlap one another around most if not all of the perimeter of side wall 58. A portion of the perforations 28 in the overlapping zones 30', 32' and 34' are also depicted in FIGS. 4 and 5 to illustrate the formation and maintenance of openings, e.g., as opening 60, extending through the side wall 58. The alignment of the perforations 28 in each overlapping zone 30', 32', 34' and 30, 32, 34 provides a multiplicity of such spaced apart openings extending completely through the side wall. Given the dimensions and spacing of the perforations 28 stated above, each opening 60 is no greater in size than the perforation width PW. The spacings in the sheet length SL and sheet width SW directions between openings 60 is dependent on the number of layers formed when the sheet 11 is unrolled into the expanded roll state to fit into the vessel lumens.

The spaced apart openings 60 are formed due to the complementary interaction of the first direction 50 with the second and third directions 52 and 54 of the elongated perforations 28 in each overlapping zone. As is evident from FIGS. 4 and 5, the alignment of the zones in the sheet length direction SL and the sheet width direction SW is not critical to the formation of the openings 60. A lateral shift or twist in the rolled up tubular body 13 is tolerable as it still allows the openings 60 to form due to the interaction of the perforations 28 extending at the +45° and −45° directions 52 and 54 in the inner layers with the 0° direction 50 in the outermost layer. The likelihood of twisting is lessened by orienting the perforations 28 in each zone in the mirror image manner depicted in FIG. 2 but may occur to a slight extent.

Although FIGS. 4 and 5 show the tubular body 13 formed of three overlapping layers, it will be understood that the tubular body diameter may be increased or decreased, thereby decreasing or increasing, respectively, the number of overlapping layers, to accommodate a larger or smaller vessel lumen diameter. When the diameter is increased and the tubular body 13 is formed with two overlapping layers (at least in part), the openings 60 may need to be spaced closer together and be somewhat smaller than the openings 60 depicted in FIGS. 4 and 5. When the diameter is decreased to a point where more than three overlapping layers are formed at least in part, the openings 60 may also be spaced further apart and be somewhat larger in size.

In this regard, the preferred embodiment of the stent described above and depicted in the drawings is preferably dimensioned to be used in blood vessels having a diameter in which the tubular body 13 is accommodated having two, three, four or five or more and any fraction therebetween of overlapping layers in its expanded roll state. A selection of stents 10 may be provided with the sheet length SL and the lengths of the perforation zones 30, 32, 34 and 30', 32', 34' tailored to accommodate a particular range of body vessel tureen diameters. A selection of such stents may also be provided having different sheet widths SW to bridge vascular defects of differing lengths in the body vessel. The physician may select the appropriately dimensioned prosthesis 10 for the particular body vessel.

Preferably the second and third directions 52 and 54 are at +45° and −45°, respectively to the 0° direction 50, and therefore extend to 90° to one another. These angels may also be varied as long as the perforations 28 extending at each angle overlie one another when the sheet 11 is rolled into the tubular body 13 and provide a suitable number of aligned openings 60 through the multiple layers of the side wall.

In the illustrated preferred embodiment, the perforation zones are arranged such that in the first half 40, the first, second and third zones 30, 32, 34 are arranged across the center line border band 46 from the second, first and third zones 30', 32', 34' of the second half 40', so that the second and third directions 52, 54 of the second and third zones 32, 32' and 34, 34' are adjacent to one another across the center border band 46 in order to balance twist biases induced in the sheet 11 by the second and third directions 52 and 54 of the elongated perforations 28. The particular order in which these zones appear from the outer-most to the inner-most layers forming the size wall of tubular body 13 may be changed from the order depicted in FIGS. 2–5. In any such configuration, the sheet 11 may be rolled up such that the first perforation zones 30, 30' are in the inner-most layer rather than the outer-most layer as shown.

Moreover, while the preferred number of perforation zones in each half is three to provide a substantially three layer, tubular body in the expanded roll state, only two or more than three such perforation zones may be provided in each half to provide substantially two or more layers in the tubular body. The case of four perforation zones in each half to provide substantially four layers in the tubular side wall in the expanded roll state, an additional pair of side by side perforation zones may be provided both having elongated perforations extending at 90° to the length direction 50 of the sheet.

In addition, the above-described preferred embodiment of the stent of the present invention is provided with perforation zones formed in portions of first and second halves of the sheet on either side of the center line area 46 to thereby form parallel rows of perforation zones along the sheet length SL. It is also contemplated that additional rows of parallel perforation zones may be formed across the sheet width SW and extending the sheet length SL. A selection of directions 50, 52, 54 (or other suitable directions) for each perforation zone is to be made to offset the above described curl bias forces induced by the perforation directions so that the tendency of the sheet to twist out of alignment with the sheet length direction or 0° direction 50 when in the expanded roll state is minimized.

Although the sheet is preferably formed of metal foil, the invention may be practiced using sheets formed of biocompatible plastic materials or other suitable sheet materials.

The prostheses of the present invention may be employed as a graft bridging an aneurysm in a blood vessel and may be employed in the system depicted in the above-referenced '906 application. The prostheses of the present invention may be used in any of a variety of alternative applications where radial support is desired or channeling of blood is desired. Repair of a tear in the intimal wall of an artery or a repair of a dissecting aneurysm is contemplated. The present invention may also be utilized as a stent, such as following radial expansion of a stenosis by balloon angioplasty, laser ablation, rotational atherectomy, or other lesion modifying technique.

Although the above described stent 10 is preferably self-expanding, it will be understood that the perforation zones and complementary pattern may also be used in multilayer sheet stents that are expanded by an expansion mechanism such as a balloon catheter from the collapsed roll state to an expanded roll state in order to provide the openings 60 through the side wall of the tubular body formed on expansion.

The perforation pattern of the present invention allows the resulting openings 60 to be relatively numerous and small enough to avoid significant blood loss therethrough. The perforation pattern of the present invention is advantageous over a theoretical perforation pattern of regularly spaced and oriented openings, e.g., equally spaced apart and sized openings over the entire sheet surface, because, in such a case, each perforation would have to be large in order to ensure that at least some portion of the perforations would coincide in the overlapping sheet layers to provide the openings therethrough. The large perforations would weaken the stent and adversely affect its effective range of expansion diameters. If the perforations were to perfectly align with one another, the openings would be too large and permit blood flow through them. In practice, the expansion of the stent to fit the body vessel lumen cannot be controlled, and so the size of the openings also cannot be controlled. The number of layers and diameter of each layer are indeterminate, and consequently, a uniform spacing pattern of perforations cannot provide the assurance that the openings will not be blocked when the stent is positioned in situ. And, it is not possible to visualize or gauge the openings in situ in order to assess the degree to which they are open. By contrast, the perforation pattern of the present invention offers significant advantages in avoiding these problems.

Although the present invention has been described in terms of certain particular aperture patterns, any of a wide variety of aperture size, shape and distribution patterns can be utilized and still accomplish the functional advantages of the present invention. In general, the aperture size and pattern should seek to produce a net aperture through the side wall of the prosthesis which is small enough to prevent substantial blood loss therethrough, and large enough to facilitate endothelial cell growth.

By "net aperture" opening, it is meant the effective cross section of the aperture which has a clear passageway through each of the two or three or four or five or more adjacent layers of the sheet when rolled up into the expanded, implanted diameter. Thus, for example, referring to FIG. 5, each slot in each of the three adjacent layers may have a width of about 0.2 mm and a length of about 3 mm. Due to the misalignment of the longitudinal axis of the overlaying apertures, the net opening 60 through the side wall 58 will be on the order of about 0.2 mm in diameter.

In general, net aperture openings of less than about 0.5 mm, preferably less than about 0.25 mm and more preferably less than about 0.10 mm are contemplated. Net aperture openings of about 0.05 mm or smaller may be preferred in some applications. The net aperture opening and aperture density preferably produce a blood or blood serum flow rate through the side wall within the range of from about 100 to about 3000 cc/cm$^2$/minute. More preferably, the leak rate is less than about 300 and preferably no more than about 250 cc/cm$^2$/minute.

Net aperture dimensions much greater than the recited ranges may also work, but may delay the time until the apertures are sealed off by natural mechanisms. This may be undesirable in an application intended for use as a vascular graft, in which excessive blood loss through the wall of the aperture may be undesirable. In addition, the net aperture distribution should be such that will permit a continuous or substantially continuous layer of endothelial cell growth along the wall of the prosthesis. At the present time, it is believed that the endothelial cell growth will travel no more than about 0.125 inches along a metal surface.

As recited supra., the minimum aperture size should be sufficient to permit endothelial cell growth therethrough. This may be accomplished in apertures having a net cross section measured in microns, with exact limits which can be established through routine experimentation by those of skill in the art. Thus, one hole pattern and distribution pattern for a porous sheet could involve the use of a laser perforation or other technique for producing hundreds or thousands or more of apertures per square centimeter. Distribution may be regular or random, as long as there exists a statistical likelihood that a continuous aperture 60 will extend through each of the adjacent wall layers in the expanded, implanted diameter, at a distance of no further apart than about ⅛ or 1/10 of an inch as has been discussed.

One advantage of the aperture configuration and patterns illustrated in FIG. 2, and other pattern designs not specifically illustrated but contemplated herein, is that an appropriate net aperture size will be achieved in the rolled implanted expanded prosthesis, throughout any of a variety of implanted diameters. Since the same stent or graft will optimally be useful in any of a range of vessel diameters, the optimal aperture pattern and distribution will permit the stent to expand from the insertion diameter to any of a variety of implanted diameters which will always achieve a net aperture distribution and dimension in accordance with the foregoing. Thus, the prothesis of the present invention is expandable from an insertion diameter to any of a variety of implanted diameters and still achieve the endothelial cell growth objectives of the present invention.

As will be appreciated by those of skill in the art in view of the disclosure herein, the embodiments which utilize zones of longitudinal slots may be provided with any of a variety of orientations with respect to each other. One consequence of certain aperture patterns is the introduction of roll bias in the final product. By roll bias, it is meant the tendency of the stent upon unwinding from the insertion diameter to the implanted diameter to unwind in a manner that spirals out in an axial direction, thereby extending the axial length of the stent. In applications where a roll bias is undesirable, perforation patterns, such as left- and right-hand mirror image patterns, have been found to assist in minimizing roll bias.

For example, although the orientation of the longitudinal slots in the multi-zone embodiment of FIG. 2 are 0° from the longitudinal axis, −45° and +45°, all longitudinal slots may alternatively be provided with the same orientation throughout the sheet. Preferably, to minimize roll bias, at least one zone or a group of zones will have an orientation of −θ to create a first roll bias, and an equivalent zone or groups of zones will have an orientation of +θ, with respect to the longitudinal axis of the sheet to create an opposite roll bias. θ may range from about 10° to about 80°, preferably from about 30° to about 60°, and more preferably from about 40° to about 50° with respect to the longitudinal axis of the sheet. Alternatively, one or more groups of apertures may comprise oval or round holes, rectangular openings, or other geometric configurations, provided that the net aperture size and distribution in the wall of the finished stent when in the intended expanded diameter satisfies the functional requirements described above.

The apertures may be provided in any of a variety of manners which will be understood to those of skill in the art. For example, a sheet of material, such as Elgiloy, or any of a variety of stainless steel or other biocompatible materials having a sufficient spring force is provided. The sheet may then be laser etched, photo etched, perforated using electronic discharge technology or other means, depending upon the sheet thickness, physical properties of the alloy or polymer sheet and desired aperture diameters and patterns. In one embodiment of the invention, the apertures are produced using conventional photo etching technology. The etched sheet is then rolled up and restrained within about a 2½ cm restraining tube, and heated to approximately 900° F. for approximately 4 hours, to relieve stress. In general, the larger the diameter of the restraining tube during the heat stress relief step, the greater the spring force in the finished prosthesis. The heat treated prosthesis may then be tightly rolled and installed within a deployment catheter, or packaged for other use at the clinical site. Prior to loading or packaging, coatings may be added to the tubular prosthesis. Anticoagulants, such as heparin, endothelial cell growth initiators, macrophage intimation inhibitors or any of a variety of other drugs or coatings, may be utilized, as will be apparent to those of skill in the art in view of the disclosure herein.

Another feature of the prevent invention is the provision of an extremely low leading edge profile in the implanted prosthesis. The leading edge profile, or radial thickness of a prosthesis wall, as seen in a direction of blood flow, is believed to cause undesirable turbulence in the bloodstream. One conventional coronary artery stent, for example, has a leading edge profile on the order of 0.007 inches. The spiral rolled construction of the present invention permits the use of very thin sheet material, which provides a relatively high hoop strength for resistance to radial compression, as a function of total wall thickness. This allows blood flow turbulence to be minimized.

For example, in a stent having a sheet thickness of about 0.0015, rolled up to have three overlapping layers and a net wall thickness of about 0.0045 in accordance with the present invention, is expected to have a hoop strength in excess of that for conventional non-rolled stents or grafts having a greater wall thickness. In general, radial deformation preferably begins within the range of from about 50 to about 750 mm Hg global radial pressure. Sheet thicknesses as low as 0.001 inches, and preferably as low as 0.0005 or less (to produce a leading edge profile of 0.0015 inches or less in a three layer as implanted prosthesis) are contemplated by the present inventor.

In addition, the tubular prosthesis of the present invention provides a relatively uniform leading edge. Many alternate stents and grafts have a jagged or angular leading edge, as a consequence of the wire construction or diamond patterns that may be cut into the wall of the prosthesis. The uniform leading edge is also believed to assist in minimizing leading edge turbulence. Blood flow turbulence may also be minimized, and compatibility of the prosthesis is optimized by the microporous apertures of the present invention, particularly when provided in a density and distribution as discussed above. The facilitation of a continuous endothelia cell coat along the interior wall of the stent is believed to make the stent appear to the blood and surrounding tissue more biocompatible than the material of the stent may otherwise appear to be.

Although the present invention has been described in terms of certain preferred embodiments, variations of the invention will become apparent to those of skill in the art in view of the disclosure herein. Accordingly, the scope of the invention is intended to be limited solely by the attached claims, and not by specific structural recitations contained herein.

What is claimed is:

1. A method of minimizing roll bias in a self-expandable tubular prosthesis, comprising the steps of:

providing a flexible sheet;

creating at least a first and a second group of apertures through the sheet; and rolling the sheet about a longitudinal axis to form a self expandable tubular prosthesis;

wherein the first group of apertures induces a roll bias component in a first direction along the longitudinal axis, and the second group of apertures induces a roll bias component in a second, opposite direction along the longitudinal axis to minimize any net roll bias in the tubular prosthesis.

2. A tubular prosthesis, comprising:

a flexible rectangular sheet, having a longitudinal axis and at least first, second, and third groups of apertures extending therethrough;

the first group comprising a first plurality of parallel slots inclined at a first angle with respect to the longitudinal axis;

the second group comprising a second plurality of parallel slots inclined at a second angle with respect to the longitudinal axis;

the first, second, and third groups of apertures arranged on the sheet such that when the sheet is wrapped about an axis through at least about three revolutions to form a tubular prosthesis, apertures from the first, second, and third groups align to produce a plurality of ports extending through the side wall of the prosthesis.

3. An intraluminal stent implantable in a body vessel lumen, comprising:

a tubular body having a side wall and an inner lumen with an axial length extending between first and second ends of the tubular body, said tubular body formed of a sheet of bio-compatible material forming said side wall and inner lumen when placed in the vessel lumen in an expanded roll state, said sheet having a sheet length providing said first and second overlapping layers when said sheet is in the expanded roll state and a sheet width corresponding to said axial length; and first and second perforation zones formed in first and second portions of said sheet displaced from one another along said sheet length, said first perforation zone having a first plurality of elongated perforations extending in parallel with one another in a first direction, and said second perforation zone having a second plurality of elongated perforations extending in parallel with one another in a second direction differing from said first direction;

wherein the first and second perforation zones substantially overlap one another when said sheet is rolled up into said tubular body having at least two layers in the vessel lumen and provide openings in said side wall through aligned portions of said elongated perforations.

4. The stent of claim 3, further comprising:

a third perforation zone formed in a third portion of said sheet along said sheet length with a third plurality of elongated perforations extending in parallel with one another in a third direction differing from said first and second directions, wherein the first, second and third perforation zones overlap one another at least in part when said sheet is rolled up into said tubular body and provide openings through said side wall at aligned portions of said elongated perforations.

5. The stent of claim 4, wherein said first, second and third perforation zones are formed inside a border band of said sheet and are separated from one another by mutual border bands.

6. The stent of claim 5, wherein said first, second and third directions are defined at first, second and third angles, respectively, with respect to said sheet length.

7. The stent of claim 5, wherein:

said first direction is at a first angle with respect to said sheet length that is substantially in parallel with said sheet length;

said second direction is at a second angle differing from said first angle; and said third direction is at a third angle differing from said first angle and said second angle.

8. The stent of claim 7, wherein:

said second angle is at about 45° to said first angle; and said third angle is at about 90° to said second angle.

9. In an intraluminal stem implantable in a body vessel lumen of the type comprising a tubular body having a side wall and an inner lumen of an axial length extending between first and second ends, said tubular body formed of a sheet of biocompatible material rolled into a plurality of layers to form said side wall and inner lumen, said sheet having a sheet length providing said plurality of overlapping layers when said sheet is rolled up in the direction of the sheet length and a sheet width corresponding to said axial length, the improvement comprising:

means for defining first and second rows extending substantially across said sheet width and along said sheet length;

in said first row, first and second perforation zones formed in first and second portions of said sheet displaced from one another along said sheet length, said first perforation zone of said first row having a first plurality of elongated perforations extending in parallel with one another in a first direction in said first row, and said second perforation zone of said first row having a second plurality of elongated perforations extending in parallel with one another in a second direction in said first row;

in said second row, first and second perforation zones formed in further first and second portions of said sheet displaced from one another along said sheet length in side-by-side relation to said first and second perforation zones in said first row, said first perforation zone of said second row having a first plurality of elongated perforations extending in parallel with one another in a first direction of said second row, and said second perforation zone of said second row having a second plurality of elongated perforations extending in parallel with one another in a second direction of said second row, such that:

said first and second perforation zones of said first row substantially overlap one another when said sheet is rolled up into said tubular body and provide openings through said side wall at aligned portions of said elongated perforations; and said first and second perforation zones of said second row substantially overlap one another when said sheet is rolled up into said tubular body and provide openings through said side wall at aligned portions of said elongated perforations.

10. The stent of claim 9, wherein said improvement further comprises:

a third perforation zone formed in a third portion of said sheet in said first row along said sheet length with a third plurality of elongated perforations extending in parallel with one another in a third direction differing from said first and second directions in said first row, such that the first, second and third perforation zones overlap one another at least in part when said sheet is rolled up into said tubular body and provide openings through said side wall at aligned portions of said elongated perforations; and a third perforation zone formed in a third portion of said sheet along said sheet length in said second row with a third plurality of elongated perforations extending in parallel with one another in a third direction different from said first and second directions in said second row, such that the first, second and third perforation zones in said second row overlap one another at least in part when said sheet is rolled up into said tubular body and provide openings through said side wall at aligned portions of said elongated perforations.

11. The stent of claim 10, wherein said first, second and third perforation zones are formed inside a border band of said sheet and are separated from one another by mutual border bands.

12. The stent of claim 11, wherein said first, second and third directions in said first row are defined at first, second and third angles, respectively, with respect to said sheet length.

13. The stent of claim 11, wherein:

said first direction in said first and second row is at a first angle with respect to said sheet length that is substantially in parallel with said sheet length;

said second direction in said first row is at a second angle differing from said first angle in said first row;

said third direction in said first row is at a third angle differing from said first angle and said second angle in said first row;

said second direction in said second row corresponds to said third angle in said first row; and said third direction in said second row corresponds to said second angle in said first row.

14. The stent of claim 13, wherein:

said second angle in said first row and said third angle in said second row are substantially at 45° to said first angle; and said third angle in said first row and said second angle in said second row are substantially at 90° to said second angle.

15. The stent of claim 14, wherein said means for defining said first and second rows comprises means for dividing said sheet into first and second halves extending lengthwise along said sheet length.

16. An intraluminal stem adapted to be introduced to a site in a body vessel in a collapsed roll state and implanted to bridge the site in an expanded roll state, the stent comprising:

a tubular body having a side wall and an inner lumen of an axial length extending in a longitudinal direction between first and second ends, the tubular body formed of a sheet of biocompatible material rolled into a plurality of overlapping layers to form the tubular body side wail and inner lumen, the sheet having a sheet width corresponding to the tubular body axial length and a sheet length providing the plurality of overlapping layers when in the expanded roll state;

a plurality of perforation zones formed in the sheet and spaced apart along the sheet length adapted to substantially overlie one another when the sheet is rolled into the plurality of layers in the expanded roll state, the perforation zones occupying substantially equal areas of the sheet; and each perforation zone further comprising a plurality of elongated perforations extending in parallel with one another at a predetermined perforation angle to the sheet length, wherein the perforation angle of the elongated perforations at each perforation zone differs from the perforation angle of the elongated perforations of other perforation zones along the sheet length, whereby the plurality of perforation zones substantially overlie one another when the sheet is rolled in the expanded roll state having a substantially corresponding plurality of sheet layers forming the tubular body side wall and provide holes extending through the tubular body side wall where portions of the elongated perforations in the perforation zone in each layer are aligned with one another to encourage the formation of neointimal growth in the tubular body lumen between the adjacent holes.

17. The stent of claim 16, wherein said plurality of perforation zones comprise first, second and third perforation zones formed inside a border band of said sheet and separated from one another by mutual border bands.

18. The stent of claim 17, wherein the plurality of elongated perforations of said first, second and third perforation zones extend in first, second and third directions, respectively.

19. The stent of claim 18 wherein:

said first direction is at a first angle with respect to said sheet length that is substantially in parallel with said sheet length;

said second direction is at a second angle differing from said first angle; and said third direction is at a third angle differing from said first angle and said second angle.

20. The stent of claim 19, wherein:

said second angle is substantially at 45° to said first angle; and said third angle is substantially at 90° to said second angle.

21. The stent of claim 16, wherein said plurality of perforation zones are formed in substantially equally sized areas of said sheet and have zone widths that substantially correspond with said sheet width and zone lengths that substantially correspond with the circumference of the tubular body when in said expanded roll state.

22. The stent of claim 16, wherein:

said plurality of perforation zones are formed in a farther plurality of M rows extending along the sheet length each row having a further plurality N perforation zones, the N perforation zones of each row located in side-by-side relationship to each other, the M×N perforation zones occupying substantially equally sized areas of said sheet separated from one another by mutual border bands and having zone widths that substantially correspond with said sheet width divided by M and zone lengths that substantially correspond with the circumference of the tubular body when in said expanded roll state of substantially N layers.

23. The stem of claim 22, wherein:

the plurality of elongated perforations in at least certain ones of the side-by-side perforation zones in each row extend at predetermined complementary angles to one another that tend to offset curl biases tending to cause the sheet to roll up out of alignment with the sheet length.

24. The stent of claim 23, wherein the N perforation zones of the M rows comprise first, second and third perforation zones having perforations extending in first, second and third directions, respectively.

25. The stem of claim 22, wherein the M rows comprise two rows and the N perforation zones in each row comprise at least first and second perforation zones separated from one another by said mutual border bands.

26. The stent of claim 25, wherein:

the plurality of elongated perforations in at least the first perforation zones in each row extend at predetermined complementary angles that tend to offset curl biases tending to cause the sheet to roll up out of alignment with the sheet length; and the plurality of elongated perforations in the second perforation zones in each row extend at angles differing from the angles of the first perforation zones in that row to provide the holes through aligned portions of the overlapping first and second perforation zones.

* * * * *

UNITED STATES PATENT AND TRADEMARK OFFICE
CERTIFICATE OF CORRECTION

PATENT NO. : 5,728,150

DATED : March 17, 1998

INVENTOR(S): Edward McDonald; Robert Rosenbluth; Rodney Brenneman

It is certified that error appears in the above-identified patent and that said Letters Patent is hereby corrected as shown below:

In Claim 16, column 16, line 51, change "side wail" to --side wall--.

In Claim 16, column 16, line 56, change "side wail" to --side wall--.

In. Claim 23, column 18, line 15, change "The stem of" to --The stent of--.

In Claim 25, column 18, line 26, change "The stem of" to --The stent of--.

Signed and Sealed this

Eighth Day of February, 2000

*Attest:*

Q. TODD DICKINSON

*Attesting Officer*     *Commissioner of Patents and Trademarks*